United States Patent [19]

Alnor

[11] 3,949,071

[45] Apr. 6, 1976

[54] METHOD AND COMPOSITION FOR TREATING BURNS AND SCALDS

[75] Inventor: Carl Christian Alnor, Haslev, Denmark

[73] Assignee: Ferraton Aktieselskab, Denmark

[22] Filed: Mar. 5, 1974

[21] Appl. No.: 448,179

Related U.S. Application Data

[63] Continuation of Ser. No. 289,641, Sept. 18, 1972, abandoned, which is a continuation-in-part of Ser. No. 876,573, Nov. 13, 1969, abandoned.

[52] U.S. Cl. .............. 424/127; 424/274; 424/315; 424/318; 424/339; 424/340; 424/DIG. 13
[51] Int. Cl.² ....................................... A61K 33/00
[58] Field of Search ............ 424/127, 315, 45, 340, 424/318, 274, 339, DIG. 13

[56] References Cited
UNITED STATES PATENTS

| | | | |
|---|---|---|---|
| 1,901,434 | 3/1933 | Cade et al........................... | 424/127 |
| 2,079,166 | 5/1937 | Grote.................................. | 424/318 |
| 2,729,586 | 1/1956 | Peck................................... | 424/318 |
| 3,412,033 | 11/1968 | Karsten et al...................... | 252/107 |

FOREIGN PATENTS OR APPLICATIONS

| | | | |
|---|---|---|---|
| 1,010,200 | 11/1965 | United Kingdom................ | 424/318 |
| 838,913 | 6/1960 | United Kingdom................ | 424/45 |

OTHER PUBLICATIONS

Chemical Abstracts, Vol. 38, 5361, (1944); Vol. 45 8653 (1951); Vol. 50, 15033–15034 (1956).
Remington's Practice of Pharmacy, 12th Ed. Mack Pub. Co., Easton, Penna., 1961 p. 1799.
Handbook of Non-Prescription Drugs, Sept. 1967 Pub. by Amer. Pharm. Assoc., pp. 70–71.

Primary Examiner—Frederick E. Waddell
Attorney, Agent, or Firm—Robert E. Burns; Emmanuel J. Lobato; Bruce L. Adams

[57] ABSTRACT

A method and a composition for treating and remedying the consequences of burns, scalds and other skin affections resulting in an acidose. An aqueous buffer solution having a pH value of 8–10, preferably 8.5–9, is applied to the affected skin areas, immediately or very soon after the burning, scalding or other affection has taken place, and the application is, if necessary, repeated or continued. Skin which has been treated in this manner does not undergo the more or less profound blistering and damaging which is otherwise inevitable after burning or scalding. The composition preferably comprises a base, a surface-active agent and a fatty acid.

3 Claims, No Drawings

METHOD AND COMPOSITION FOR TREATING BURNS AND SCALDS

CROSS REFERENCE TO RELATED APPLICATIONS

This application is a continuation of Ser. No. 289,641 filed Sept. 18, 1972, now abandoned, which is a continuation-in-part of Ser. No. 876,573 filed Nov. 13, 1969, now abandoned, which is entitled COMPOSITION AND PROCESS FOR TREATING BURNS AND SCALDS. The contents of this application is incorporated herein by reference.

BACKGROUND OF THE INVENTION

The present invention is concerned with a method and a composition for treating burns, scalds and other skin affections having similar effects on the skin.

When the skin has been exposed to strong heat, caused by fire, scalds, contact with hot articles or exaggerated exposure to the sun, a patho-physiological process is started by the organism itself, and this process is the cause of progressively increasing damages occurring during the first four to seven hours or, in severe cases, even up to 24 hours after the exposure of the skin to the action of heat. These damages involve erythema of the skin, in the case of first degree burn, blisters in the case of second degree burn, and damaged tissue at a deeper level described as third degree burn, which may be associated according to the severity with oedema of a superficial or deep nature, and in severe cases with reduction of blood pressure, toxicity and shock.

Hitherto, the most effective means to prevent or to substantially inhibit these secondary consecutive symptoms of acute burns has been the immersion of the involved body part into standing water of a temperature not exceeding 25°C.; in this treatment, the immersion of the burned part of the body should be maintained as long as the spontaneous pain persists (cfr. Modern Treatment, Vol. 4, No. 6, November 1967). However, the water treatment suffers from some rather serious drawbacks. Firstly, it is not always as effective as would be desirable. Secondly, the layman does not have too much faith in the effectiveness of a simple water treatment, for which reason a large proportion of burns and scalds which could have been treated by the water treatment with some beneficial result is left untreated; thirdly, the water used may not be as sterile as necessary to ensure that no infections with organisms originating from the water are incurred in addition to the burning or scalding. Fourthly, not all burnt parts of the body can in practice be immersed in water for a long period of time, and fifthly, standing water of the necessary purity and of the suitable temperature is not always easily available for treatment immediately after the burning has occurred, e.g. in the case of car accidents in deserted localities. Accordingly, a remedy in the form of an easily handled and easily applicable preparation for effective, immediate treatment and use at home, at work, and, e.g. for having available at an easily accessable place in the car, would be highly desirable.

SUMMARY OF THE INVENTION

The method of the invention for treating skin which has been affected by burning, scalding or other affections causing similar effects comprises applying to the affected skin areas an aqueous buffer solution of a pH value of 8–10.

It has been found that when such a solution is applied to the skin after burning or scalding or other exposure to extreme action of heat, preferably immediately thereafter, and the application is, if necessary, repeated or continued during the first hours after the exposure to heat, the usual reactions of the affected skin, such as swelling and blistering and the more or less profound damages of the skin resulting therefrom, do not occur; in most cases, no undesirable consequences at all of the action of heat or, at the most, a flush or a slight peeling of the chorion skin will occur.

DETAILED DESCRIPTION OF THE INVENTION

The method of the invention may be used both for the general remedy of burns and scalds and for cosmetic purposes, for example for remedying the cosmetic problems caused by exaggerated sunbathing. It may also be used for remedying the skin irritation and pain resulting after other affections causing similar effects, such as intense rubbing of the skin (e.g. rubbing of the heel skin in too small shoes), insect stings, e.g. bee stings, and mosquito, and attacks, and nettle and red jellyfish stings or stinging.

According to a preferred embodiment of the invention burns and scalds or other similar affections are treated by applying to the burnt or scalded or otherwise affected skin, immediately or soon after the burning or scalding or other affection causing similar effect has taken place, a buffer solution having a pH value of 8–10. According to an especially preferred embodiment of the method, the application is repeated every time the pain returns. It is highly preferred that the application of the buffer solution is started within about 5 minutes from the burning or scalding accident, but satisfactory results may also be obtained in cases where the application of the buffer solution is started not later than half an hour after the burning or scalding accident and, in special cases, even up to four hours after the burning or scalding accident, depending upon the degree of heat to which the skin has been exposed.

In the case of sun burns, however, treatment with the buffer solution according to the method of the invention will be effective even if started as late as 12 – 24 hours after the exaggerated exposure of the skin to sunlight. Quite generally, however, it can be said that the method of the invention is the more effective, the sooner the application of the buffer solution is started.

The present invention revolutionizes the treatment of burns, including sunburns, and scalds. The following novel theory accounts for the surprising result of the present treatment, however, the following hypotheses are not to be construed as limiting the invention:

It is believed that the aqueous buffer solution of pH value 8–10 functions by counteracting or neutralizing a kind of an acidose which is produced in the affected skin by the organism. This acidose is believed to be the true cause of the progressively increasing skin damages occurring during the first hours after the exposure to extreme action of heat, in that it causes a change of osmotic pressure, which change leads to increased production of histamine, which again leads to increased production of $\gamma$-globulin. When the skin is treated with a aqueous buffer solution of pH value 8–10, sufficiently soon after the exposure to heat, and the treatment is repeated or continued to the extent necessary (until the pain in the skin does not return), the otherwise progressively proceeding process stops, and, accordingly, the skin does not undergo the more or less profound damages with their well-known consequences which are otherwise inevitable after burning or scalding. In fact, experience has shown that nearly all burns and scalds start as first degree burns immediately on extreme exposure to heat and thereafter, if the action of heat was sufficiently grave, develop into second and third degree burns because of the malign condition produced by the organism itself, the severity of the final degree of burn and the rate at which this final degree is reached being dependent on the severity of the action of heat. In accordance with this, a burn, if immediately and effectively treated according to the invention, does not develop into a second or third degree burn; the process will stop at a stage where little or no serious damage of the tissue has taken place.

In a similar manner as burns and scalds, also the other above-mentioned skin affections, which have been shown to be of a kind giving rise to an acidose in the affected skin, can be effectively treated by the method of the invention.

The method of the invention has been thoroughly investigated in pilot tests and auto-trials without any indication of side effects. The present method is much more effective than water treatment; and it may be carried out using a composition (i.e. an aqueous buffer solution) which is easily applied and easily handled. Such composition, therefore, constitutes an indispensable and ideal "household remedy", which may always be kept available and ready in e.g. homes, factories, laboratories, and cars for immediate treatment when a burn or scalding accident has taken place. The treatment of the patient according to the method of the invention after burning or scalding or similar affection of the skin is the only medical aid where immediate self-treatment or other "on the spot"-treatment is justified and recommendable without a preceding diagnosis by a doctor.

As stated above, the pH value of the aqueous buffer solution if 8–10. Compositions having a higher pH value may be very fast acting and thus useful for special purposes, but with such compositions, it is generally necessary to take precautions to avoid caustic etching of the skin. At pH values below 8, the effect of the composition is less pronounced. For general use, a pH value of 8.5–9 has been found most satisfactory.

Due to the buffer effect, prolonged action at an effective pH value is obtained, which not only reduces the number of necessary applications to the skin, but also seems to warrant an especially effective neutralization of the malign acidose conditions.

The buffer solutions of pH value 8–10 for use in the method of the invention may be prepared in a wide variety of specific forms in accordance with the intended application method and other practical considerations. Thus, for use in hospital emergency rooms and for quick and efficient treatment of burns and scalds of larger skin areas, the buffer solution may be provided simply in the form of a liquid into which the affected skin area or the whole body of the patient is immersed. After a suitable period in such a liquid, further treatment, if necessary (depending on the pains), or if desired, may be performed using other application forms of the composition of the invention.

For general household use and for use in e.g. factories or laboratories, however, the buffer solution of the invention is suitably prepared in the form of a viscous, "fatty" liquid or cream which is easily rubbed into the skin; it may also be prepared in the form of an aerosol foam composition.

The preparation of buffer solutions having a pH value of 8–10 may be performed using suitable acids and bases in many possible ways obvious to one skilled in the art, but according to the invention, the buffer solutions are suitably prepared from a base and a fatty acid of the type occurring naturally in the form of glycerol esters in fats and oils, or a mixture of such fatty acids as the principal constituents. In a preferred embodiment, also a surface-active agent is included. The surface-active agent and the fatty acid contribute to render the solution "skin-penetrating", that is, capable of effectively wetting and penetrating the skin. A pH value in the range of 8–10 may be secured by proper choice of constituents and the ratio between the constituents. The viscosity of the composition may be adjusted to the desired value by means of thickening agents or by proper choice of the water content of the composition.

As the base, alkali metal bases are well suited, and especially sodium carbonate has been found to give excellent results, but also many other bases which can be used to form a buffer system in the pH range stated may be suitable, e.g. ammonium carbonate, $Na_2HPO_4$ and the like. Stronger bases such as alkali metal hydroxides, particularly sodium hydroxide, alkali metal phosphates, such as $Na_3PO_4$, alkali metal and ammonium salts inclusing alkali metal hydrogen borates may also be used. The base must, of course, be physiologically acceptable in the buffer solution. Physiologically accepted amines can also be used including trialkylamines such as triethyl amine, and other amines such as dibenzylamine and N-benzyl-$\beta$-phenethylamine. It is also possible to use salts of fatty acids e.g. sodium oleate and oleic acid instead of forming this system by adding the sodium base to the oleic acid, and analogously, the other alkali metal salts of the fatty acid may be used as the base.

As surface-active agents which have proved suitable for the purpose of the invention may be mentioned anionic agents based on alkyl aryl sulphonates, optionally having a content of non-ionic type, such as nonyl phenol ethylene oxide, and anionic agents based on fatty alcohol sulphates, including fatty alcohol ether sulphates. Among the suitable surface active agents can be mentioned such agents as are ordinarily used in compositions soothing to the skin, e.g. shampoo or foam bath compositions. As specific examples of suitable surface-active agents may be mentioned a product sold under the trademark COMPROX, which is based upon sodium alkyl aryl sulphonate with a content of nonyl phenol ethylene oxide, and a product sold under the trademark TEXAPON (sold by Dehydag, Federal Republic of Germany), which is based upon sodium lauryl ether sulphate. It is, however, contemplated that any physiologically acceptable surface-active agent, including agents of the anionic, cationic, non-ionic and amphoteric type, may be used for preparing the composition of the invention. Suitable surface-active agents are described for example in Encyclopedia of Surface-Active Agents, I. P. Sisley, Chemical Publishing Co., Inc., New York, N.Y., and Surface-Active Agents, A. M. Schwarts and J. W. Perry, Interscience Publishers, Ind., New York, N.Y.

As examples of fatty acids which may be used in the compositions of the invention may especially be mentioned unsaturated carboxylic acids having 16 to 20 carbon atoms, for example linoleic and linolenic acid and oleic acid. Among these, oleic acid is preferred. Also suitable are coconut oil fatty acids. Especially suitable for use in the compositions of the invention is a mixture of liquid fatty acids containing oleic acid predominantly; a product of this type is sold under the name ELAINE.

It may be desirable also to include certain other compositions in the composition of the invention, e.g. a skin-comforting ingredient such as a skin-comforting oil, for example paraffin oil; diethyl ether or another suitable physiologically acceptable volatile substance, which due to its evaporation cools the skin; a physiologically acceptable disinfectant, e.g. eugenol or aetheroleum caryophylli, which also among other things can disinfect the other components of the composition; and chlorophyll, which is believed to cause pigment production and thus contribute to the formation of a secondary protectant in the skin. Also a suitable local anaestetic such as thesit (dodecyl alcohol polyoxyethylene ether) or lidocaine may be included.

The specific proportions of base and fatty acid are dependent on the specific compounds used. The critical requirement is that the components of the present mixture must be present in a proportion which yield a solution having a pH of 8–10. If the surface-active agent takes part in the buffer system, the particular amount present may also be a determining factor as to the amount of acid and base required.

A preferred embodiment of the composition of the invention may be prepared by adding with agitation a base to a mixture of an aqueous solution of a surface-active agent and a fatty acid, and continuing the stirring until a clear solution having a buffer effect at a pH value of 8–10 is obtained. In a preferred embodiment the surface-active agent is present in an amount of about 45–75% by weight, more preferably about 50–65% by weight based on the weight of the mixture of base, fatty acid and surface-active agent.

As the base, preferably sodium carbonate is used. Other optional components, e.g. diethyl ether, eugenol and chlorophyll, are suitably added after the formation of the clear buffer solution. As surface-active agent of predominantly anionic type preferably agents of the above-mentioned types are used.

The composition and the method according to the invention are further illustrated by the following example:

Components:
| | |
|---|---|
| TEXAPON Extrakt N 40 (a mild commercial soothing surface active agent which is an aqueous solution containing about 27–28% by weight of sodium lauryl ether sulfate. The content of inorganic salt is 3% by weight and the pH of the solution is 6.4–7.0. This commercial product is usually used for preparing e.g. cosmetics or shampoo or foam bath compositions) | 5 kilograms |
| Elaine (a mixture of liquid fatty acid containing oleic acid predominantly) - | 200 grams |
| Na$_2$CO$_3$ | 700 grams |
| Diethyl ether | 100 grams |
| Eugenol (or aetheroleum caryophylli) | 2 grams |
| Chlorophyll | 0.065 gram |

The TEXAPON and the elaine are mixed, and the sodium carbonate is added to the stirred mixture of TEXAPON and elaine. The stirring is continued until a clear solution is obtained. Thereafter, the other components are added. Instead of TEXAPON, other surface active compositions may be employed in the above mixture among which COMPROX HC 20, COMPROX HC 10, HC 30 or HC 40 are particularly suitable. The comproxes are concentrated aqueous solutions of mild surface-active agents which are soothing to the skin.

The preferred composition prepared according to the above example has an excellent stability, even at high and low shelving temperatures.

The results of various tests prove the effect of the composition of the invention. Thus, two groups of rats were shaved on their backs and the bare skin immersed into hot water for various periods of time. In one series of tests, the following combination of water temperature and immersion time were used:

| | | |
|---|---|---|
| 70°C./5 sec. | 80°C./5 sec. | 90°C./5 sec. |
| 70°C./20 sec. | 80°C./20 sec. | 90°C./20 sec. |

Thereafter, the rats of one group were treated with a composition according to the example, while the rats of the other group were treated with standing tap water at 25°C., After a healing period of 5 – 14 days, all the rats of the treated group had recovered (the crusts had loosened), whereas not all of the rats exposed to the water at 90°C. and treated only with tap water survived.

In another test, water having a temperature of 85°C. was poured over the naked skin of a person's hand. The amount of hot water was about 300 cc., and it was added slowly, in the course of about a minute, from a heat-insulated container. The scalded area was kept wet and untreated for 5 minutes. Then, a composition according to the example was applied. There was pain relief immediately upon the first application of the composition. When the applied composition had dried out (approximately 10 – 15 minutes) a new application was made, necessitated by the increase in pain. Immediately after each application there was, again, pain relief. In this manner, repeated applications were made during the first hour subsequent to the scalding. Thereafter, the rest of the applied solution could be washed out with cold water, and there was no longer pain in the scalded area. There remainded an area which was somewhat red, but which showed no blistering at all, and in which there was no pain. In the course of three days, the scalded area became more dark pigmented, and during the next fortnight, the pigmentation gradually disappeared. No scars appeared in the area. This is a typical example of auto-trial.

Having thus described my invention, what I desire to secure by Letters Patent and hereby claim is:

1. A method for counteracting acidosis in the skin resulting from dermal irritation by burns, scalds, abrasions and stings which comprises applying to the affected areas an effective amount of a physiologically acceptable aqueous buffer solution having a pH value of 8–10 and comprising diethyl ether; eugenol; chlorophyll; an alkali metal carbonate base; an unsaturated fatty acid mixture comprising primarily oleic acid and a physiologically acceptable anionic surface-active agent comprising sodium lauryl ether sulfate; said surface-active agent being present in an amount of about 45–75% by weight, based on the weight of the base, fatty acid and surface-active agent, and the base and the fatty acid being present in such proportions as to provide said solution with a pH value of 8–10, thereby neutralizing said acidosis, also the weight ratio between surface-active agent, oleic acid, alkali metal carbonate and water in the aqueous buffer solution being about 14:2:7:35.

2. The method of claim 1 wherein the pH of the aqueous buffer solution is 8.5 – 9.0.

3. The method of claim 1 wherein the alkali metal base is sodium carbonate.

* * * * *